United States Patent [19]

Hugl et al.

[11] Patent Number: 4,723,020

[45] Date of Patent: Feb. 2, 1988

[54] CHROMOGENIC AMINO ACID ESTERS AND PEPTIDE ESTERS

[75] Inventors: Herbert Hugl, Bergisch Gladbach; Eugen Schnabel, Wuppertal, both of Fed. Rep. of Germany

[73] Assignee: Miles Laboratories, Inc., Elkhart, Ind.

[21] Appl. No.: 710,623

[22] Filed: Mar. 11, 1985

[30] Foreign Application Priority Data

Apr. 6, 1984 [DE] Fed. Rep. of Germany ....... 3413077

[51] Int. Cl.$^4$ ................... C07D 231/56; C07D 275/04
[52] U.S. Cl. ....................................... 548/207; 435/23; 530/328; 530/329; 530/330; 530/331; 548/371
[58] Field of Search ................ 548/207, 371; 530/328, 530/329, 330, 331

[56] References Cited

FOREIGN PATENT DOCUMENTS 39880 5/1981 European Pat. Off. .
1128371 9/1968 United Kingdom .

*Primary Examiner*—Richard L. Raymond
*Attorney, Agent, or Firm*—Roger N. Coe

[57] ABSTRACT

The present invention relates to new chromogenic amino acid esters and peptide esters of hydroxybenzo(iso)thiazoles and hydroxybenzopyrazoles, processes for their preparation and the use of the new esters as substrates for the analytical detection of esterolytic and/or proteolytic enzymes, for example in body fluids, the esters being incorporated into test agents, in particular test strips, in a suitable manner. The new esters are preferably used for the detection of leukocytes, in particular in urine.

6 Claims, No Drawings

CHROMOGENIC AMINO ACID ESTERS AND PEPTIDE ESTERS

The present invention relates to new chromogenic aminoacid esters and peptide esters of hydroxybenzo(iso)thiazoles and hydroxybenzopyrazoles, processes for their preparation and the use of the new esters as substrates for the analytical detection of esterolytic and/or proteolytic enzymes, for example in body fluids, the esters being incorporated into test agents, in particular test strips, in a suitable manner. The new esters are preferably used for the detection of leucocytes, in particular in urine.

The detection of leucocytes in body fluids, in particular in urine, is of great importance in the diagnostics of diseases of the kidneys and of the urogenital tract. This detection was originally carried out by counting the leucocytes in the non centrifuged urine or in the urine sediment. In both methods, only intact leucocytes can be recorded. However, it is known that the rate of leucocytelysis is subject to wide variations, depending on the urine medium; thus, for example, in strongly alkaline urines the leucocyte half-life is only 60 minutes. This means that the leucocyte counts determined are too low. Apart from this lysis error, quantitative microscopic determination of the leucocytes in the noncentrifuged, homogenised urine gives very accurate values in the counting chamber. Nevertheless, this method is only rarely used in practice, since it is laborious and time-consuming and requires trained personnel.

The preferred process for leucocyte determinations in the urine in medical practice was therefore the so-called field of view method in the urine sediment. For this, the sample (sediment) first had to be obtained by centrifugation. However, other constituents of the urine were also thereby concentrated, and these—such as, for example, salts and epithelial cells—make microscopic counting of the leucocytes considerably more difficult. A varying sediment content, inhomogeneities of the sediment and a different optical design of the microscopes led to relatively large errors (up to several hundred percent) in stating the leucocyte count.

In order to avoid these difficulties, several attempts have already been made to use enzymatic reactions as the detection principle for leucocytes in various body fluids, since leucocytes have a widely spread enzyme spectrum.

Thus, for example, agents for the detection of leucocytes in body fluids are known from German Offenlegungsschriften (German Published Specification) 2,826,965 and 2,836,644, in which the esterolytic and/or proteolytic activity present in the leucocytes is utilised for analytical purposes. Sulphonphthalein esters or azo dyestuff esters are used as substrates for the leucocyte esterases and/or proteases. The dyestuffs released in the enzymatic reaction are then determined by known methods. However, the agents described in these publications are still too insensitive for practical purposes, since their reaction times are too long with low leucocyte concentrations.

Various methods for the detection of proteases and esterases are also known from histochemical and cytochemical enzymology (compare, for example, A.G.E. Pearse, Histochemistry, Theoretical and Applied, 3rd edition, Churchill Livingstone, Edinburgh-London-New York 1968). In general, colourless or slightly coloured esters are used for the detection, these being split by the enzymes into a colourless acid and a similarly colourless alcohol (phenol) component. The phenol component is then converted into coloured oroducts in a subsequent reaction, for example by coupling with diazonium salts or by oxidation. F. Schmalzl and H. Braunsteiner, for example, describe in Klin. Wschr. 46, 642 (1968) a specific cytochemical leucocyte esterase detection with naphthol-AS-D-chloroLe acetate as the substrate and a diazonium salt which forms a coloured azo compound with the naphthol liberated.

However, two-component systems of this type have proved to be unsuitable for rapid and simple detection of leucocytes in body fluids, such as, for example, in the urine, since they are much too insensitive: samples containing 5,000 leucocytes/$\mu$l still do not give a reaction.

British Patent A-1,128,371 and European Patent A 12,957 describe the use of indoxyl and thioindoxyl esters as chromogenic substrates for the detection of hydrolytic enzymes in body fluids. On enzymatic cleavage of the substrate, free indoxyl is formed, which is subsequently oxidised to the easily detectable blue dyestuff indigo. A commercially available test based on European Patent A12,957 consists of a strip of filter paper impregnated with N-tosyl-L-alanine L-indoxyl ester. When the test strip is immersed in a urine sample containing leucocytes, it turns blue in colour. However, the long waiting time (about 15 minutes) before the end colouration is reached and the test can be evaluated is a considerable disadvantage of this product.

European Patent A-14,929 describes various accelerators (pyridine derivatives; imidazole derivatives; alcohols; metal complexes) for the enzymatic cleavage reaction. However, the relatively long time before complete oxidation of the indoxyl and the low sensitivity of the test (detection limit: a few thousand leucocytes/$\mu$l) remain a disadvantage. The same applies to the use of esters of leuco-indoanilines as substrates for leucocyte enzymes according to European Patent A-34,323.

European Patent A-39,880 provides a combination of the substrates according to European Patent A-12,957 and 14,929 with the detection principle of coupling with diazonium salts which has been discussed above. Although it is possible considerably to reduce the detection limits for leucocytes in this manner, the detection of 15–20 leucocytes/$\mu$l which is desired for use in practice is still not achieved. The object of the present invention was thus to discover new chromogenic substrates for ester-cleaving enzymes, which combine a high detection sensitivity with rapid cleavage by leucocyte enzymes and a rapid and intensive colour reaction with diazonium salts. This object is achieved with the esters according to the invention.

The invention relates to compounds of the general formula (I): R

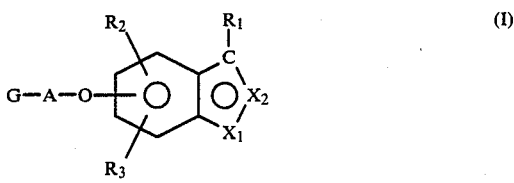

in which $X_1$ and $X_2$ are identical or different and denote nitrogen or sulphur, with the proviso that $X_1$ and $X_2$ do not simultaneously represent sulphur;

R₁ represents hydrogen or an optionally branched alkyl group which has 1 to 6 carbon atoms and can optionally be substituted by halogen or hydroxyl;

R₂ and R₃ are identical or different and represent hydrogen, $C_1$–$C_6$-alkyl groups, $C_1$–$C_6$-alkoxy groups, $C_1$–$C_6$-acyl groups, halogen, trifluoromethyl, nitro, $SO_3H$, cyano, $C_1$–$C_8$-acylamino groups, C1-C6-dialkylamino groups or $C_6$-$C_1$-aryl groups, which can in turn be further substituted by $C_1$–$C_6$-alkyl groups, $C_1$–$C_6$alkoxy groups, halogen, cyano, nitro, trifluoromethyl, $SO_3H$, $C_1$–$C_6$-acyl groups or $C_1$–$C_6$-dialkylamino groups, or R₂ and R₃ toge.her form a fused-on aromatic ring, preferably a benzene ring, which can in turn be substituted by 1 or 2 radicals R₂;

A denotes an aminoacid radical or peptide radical, and

G represents hydrogen or, preferably, a nitrogen-protective group which is usual in peptide chemistry or derived from such a group;

The invention also relates to a process for the preparation of the esters according to the invention, which is characterised in that a phenol of the general formula-(II):

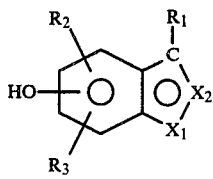

(II)

in which

X₁, X₂, R₁, R₂ and R₃ have the abovementioned meaning, is reacted with aminoacids or peptides of the general formula (III):

G-A-OH (III)

in which

G and A have the abovementioned meaning, or suitable reactive derivatives thereof, by methods customary in oeptide chemistry.

Examples of suitable reactive derivatives are the acid chlorides and the mixed anhydrides usually employed in peptide synthesis, for example with ethyl chloroformate, or activated esters, such as, for example, pentachlorophenyl esters or N-hydroxybenzotriazole esters.

The invention furthermore relates to an agent for the detection of esterolytic and/or proteolytic enzymes, containing (a) a chromogenic enzyme substrate, (b) a diazonium salt, if appropriate (r) a buffer, and if appropriate (d) a carrier and/or customary additives, characterised in that the chromogenic enzyme substrate is a compound according to the invention.

Finally, the invention also relates to a process for the detection of esterolytic and/or proteolytic enzymes in liquid samples, in particular body fluids, which is characterised in that the sample is brought into contact with the agent according to the invention and the colour reaction which occurs is determined. According to the invention, preferred compounds of the general formula (I) are those in which X₁ represents sulphur or nitrogen and X₂ represents nitrogen. Particularly preferably, X₁ represents sulphur and X₂ represents nitrogen. Compounds which are furthermore preferred are those
in which R₁ represents hydrogen and R₂ and R₃, which are identical or different, represent hydrogen, $C_1$–$C_2$-alkyl, $C_1$–$C_2$-alkoxy, halogen, $C_1$–$C_4$-dialkylamino groups or benzene radicals.

R₂ and R₃ particularly preferably represent hydrogen.

The radical G-A-0- is preferably in the 5-position in the compounds of the general formula (I).

Finally, G-A- preferably represents a radical of the general formula (IV)

in which

R₄ represents hydrogen or an optionally branched alkyl, cycloalkyl or aralkyl radical which has 1 to 15 carbon atoms, preferably 1 to 9 carbon atoms, and is optionally substituted by one or two, in particular one, hydroxyl, mercapto, carboxyl, amino o quanido group, and R₅ represents hydrogen or, preferably -CO-alkyl, -CO-aralkyl, -CO-aryl, -SO₂-alkyl or -SO₂-aryl, the alkyl radicals being straight-chain or branched radicals with 1 to 9 carbon atoms, preferably 1 to 6 carbon atoms, and the aryl radicals preferably containing 6 to 12 carbon atoms, preferably 6 carbon atoms and optionally being substituted by $C_1$- to $C_4$-alkoxy groups or halogen.

G-A- particularly preferably represents a radical, provided with a customary nitrogen-protective group, of a naturally occurring aminoacid or of a peptide of 2 to 8 such aminoacids.

The aminoacid radicals can be in their L- or D-form or in their racemic form here. Particularly preferred radicals are those of glycine, alanine, valine, leucine, isoleucine, phenylalanine and tyrosine, the Lform being particularly preferred in each case. Any free hydroxyl group present can be acylated, preferably acetylated.

A peptide radical in the definition of A is to be understood as meaning, for example, di-, tri-, tetra- and pentapeptides, preferably di- and tri-peptides, preferred possible aminoacid components being the abovementioned aminoacids.

Examples which may be mentioned of nitrogen-protective groups, in the definition of G, which are customary in peptide chemistry are the known alkyl- and aralkyl-oxycarbonyl, alkyl- and aralkyl-oxythiocarbonyl, sulohonyl, sulphenyl, vinyloxycarbonyl, cyclohexenyloxycarbonyl, ohosphoryl or carbamyl groups.

The phenols of the general formula (II) are known per se or can be prepared by known processes.

Preparation processes for the phenols of the formula (II) are describeJ, for example, in the following literature references: Franke et al., Arzneimittel-Forschung, 30 (11), 1831-1838; German Patent A-2,704,793; Davies, Soc. 1955, 2412; Ccarke et al. Condensed Isothiazoles, Part 7, J. Chem. Res., Synop., (6) 197 (1980) and Hydroxyindazole in The Chemistry of Heterocyclic Compounds, Volume 22, pages 336-340, Edited by R.H. Wiley.

The compounds according to the invention can be prepared from the phenols (II) and the aminoacids or peptides of the general formula (III) or reactive derivatives thereof (in particular the acid halides or activated esters) by synthesis methods which are known per se from peptide chemistry. Processes of this type are described, for example, in the following publications (and the literature references quoted therein): Janoff et al., Proc. Soc. Exper. Biol. Med. 136, 1045–1049 (1971); Sweetman et al., J. Hist. Soc., 22, 327–339; Jakubke et al., Chem. Ber. 100, 2267–2372 (1967) and, in particular, HoubenWeyl, Methoden der organischen Chemie (Methods of Organic Chemistry), Volume XV/1 and XV/2.

The agents according to the invention for the detection of esterolytic and/or proteolytic enzymes contain, in addition to the chromogenic substrates according to the invention, a diazonium salt of the general formula (V)

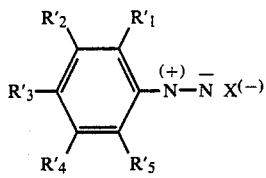

(V)

in which
R'$_1$ denotes a lower alkyl, a lower alkoxy, a lower alkylmercapto, a hydroxy, nitro, cyano, trifluoromethyl, $C_1$–$C_8$-alkylsulphonamido, arylsulphonamido, $C_1$–$C_8$-alkylsulphone, arylsulphone, sulphonic acid or carboxylic acid, an N-morpholino, an N-thiomorpholino, an N-pyrrolidino, an optionally N'-alkylated N-piperazino or N-piperidino group, halogen or hydrogen, R'$_3$ denotes a lower alkyl, a lower alkoxy, an aryloxy, a lower alkylmercapto, alkylamino or dialkylamino, a hydroxyl, nitro, cyano, $C_1$–$C_8$-alkylsulphonamido, arylsulphonamido, $C_1$–$C_8$-alkylsulphone, arylsulphone, sulphonic acid or carboxylic acid, an N-morpholino, N-thiomorpholino or N-pyrrolidino, an optionally N'-alkylated N-piperazino or N-piperidino or phenylamino group, a phenyl group which is optionally substituted by a lower alkyl or lower alkoxy radical, halogen or hydrogen, R'$_2$, R'$_4$ and R'$_5$, which can be identical or different, each denote a lower alkyl, a lower alkoxy, nitro, $C_1$–$C_8$-alkylsulphonamido, arylsulphonamido, $C_1$–$C_8$-alkylsulphone, arylsulphone, sulphonic acid or carboxylic acid or a lower alkyl mercapto group, halogen or hydrogen, and X denotes a stabilising anion, it being possible for in each case 2 adjacent radicals R$_1$ to R$_5$ to be cyclised to form a benzene ring which is optionally substituted by halogen, a $C_1$–$C_6$-alkyl, a $C_1$–$C_6$-alkoxy or a nitro, sulphonic acid or carboxylic acid group, so that a diazonium salt of the naphthalene series is formed.

Preferably, in the general formula (V) R'$_1$ represents $C_1$- to $C_4$-alkyl, $C_1$–$C_4$-alkoxy; hydroyl, nitro, halogen or hydrogen, R'$_3$ represents a $C_1$- to $C_4$-alkyl, $C_1$–$C_4$-alkoxy, aryloxy, $C_1$–$C_4$-alkylamino nitro, $C_1$–$C_4$-alkylsulphonamido, arylsulphonamido, $C_1$–$C_4$-alkylsulphone, arylsulphone, N-morpholino, N-pyrrolidino, phenylamino or sulphcnic acid group or hydrogen; and R'$_2$, R'$_4$ and R'$_5$, which can be identical or different, represent $C_1$- to $C_4$-alkyl, $C_1$- to $C_4$-alkoxy, $C_1$- to $C_4$-alkylamino, $C_1$- to $C_4$-dialkylamino, nitro, $C_1$- to $C_4$-alkylsulphonamido, arylsulphonamido or sulphonic acid groups, halogen or hydrogen.

In each case 2 adjacent radicals R'$_1$ to R'$_5$ can here be cyclised to give a benzene ring which is optionally substituted by halogen or a $C_1$- to $C_4$alkyl or $C_1$- to $C_4$-alkoxy or a nitro or sulphonic acid group.

In the context of the formula (V), aryl in each case represents an aromatic radical which has 6 to 12 C atoms, preferably 6 C atoms, and is optionally substituted by halogen or a $C_1$–$C_4$-alkyl or $C_1$–$C_4$-alkoxy group.

The diazonium salts of the general formula (V) are known per se, or they can be prepared by methods which are known per se (Houben-Weyl, Methods of Organic Chemistry, volume X/3).

The agents according to the invention preferably contain substances which accelerate the cleavage of the chromogenic substrate (I) by the enzymes to be detected. Examples of possible such accelerators are the compounds described in European Patent A-14,929, aliphatic alcohols with 8 to 25 carbon atoms, preferably 10–20 carbon atoms, which can optionally be unsaturated, being preferred. Examples of such preferred accelerators are n-decanol, n-dodecanol and, in particular, n-undecanol. Particularly preferred accelerators are homopolyaminoacids or copolyaminoacids containing basic aminoacids (E. Katchalski in: Advances of Protein Chemistry 13, 243–493 (1958); and C.B. Anfinsen, M.L. Anson, J.T. Edsall and K. Bailey (Editors); Academic Press. Inc. Publishers, New York,N.Y.) and sequential polyaminoacids. Possible basic aminoacids are those aminoacids which carry amino or guanido groups in the side chains. These are, in particular, lysine and ornithine, as well as arginine, and also basic aminoacids which are not naturally occurring, such as, for example, diamirobutyric acid, diaminopropionic acid or diaminopimelic acid. The constituent aminoacids can be in the racemic or ootically active D- or L-form in the polyaminoacids. The molecular weights (number-average) of the polyaminoacids are 1,000–2,000,000, and are preferably between 5,000 and 500,000. The contents of basic aminoacids can be between 5 and 100 mole%, preferably between 20 and 100 mole%.

The accelerators are preferably used in amounts of 0.5 to 10% by weight, preferably 1–5% by weight, of the impregnating solution in the production of the test devices described below.

The agents, according to the invention, for the detection of proteolytic enzymes and, in particular, leucocyte enzymes preferably contain a suitable buffer system. Possible systems for this purpose are, for, example, phosohate, borate, carbonate/bicarbonate, carbonate, barbiturate, tris-(hydroxymethyl)-aminomethane (=tris), 2-amino-2-methyl-propane-1,3-diol (=amediol) or aminoacid buffer, the pH value and capacity as a rule being chosen such that a pH value of 6–10, preferably of 7–9, is established in the measurement solution or on the test strip.

The agents according to the invention can also contain detergents which are known per se, since a more homogeneous colour distribution and a more intensive colouration can thereby be achieved. Possible detergents are both cationic and anionic detergents, and also amphoteric and nonionic detergents. Examples of these which may be mentioned are benzyl-dimethyl-tetradecylammonium chloride, Na dodecyl-sulphate, zephirol, polyvinylpyrrolidone, the polyaminoacids mentioned above as activators, heparinoid and mixtures of these compounds.

In the agents according to the invention, the reagents described above are preferably incorporated in an inert carrier of the type which is known per se, particularly preferred carrier matrices being porous materials, such as, in particular, filter paper, and also membranes made of plastic, glass-fibre mats (U.S. Patent Specification 3,846,247), porous ceramic strips, synthetic non-woven fibres, spongy materials (U.S. Patent Specification 3,552,928), felt, textiles, wood, cellulose or silica gel.

For this purpose, the carriers mentioned are impregnated with a solution of the reagents described above in a suitable solvent which can easily be removed, for example water, methanol, ethanol, acetone, dimethylformamide or dimethylsulphoxide. This is preferably effected in two separate steps: the material is first impregnated with an aqueous solution containing the buffer and other water-soluble additives. It is then impregnated with a solution of the chromogenic enzyme substrates of the general formula (V) and activators. However, the impregnation can also be carried out in another sequence, or with a different composition of the two impregnating solutions. Preferably, the impregnating solution or the fluid to be investigated contains the compounds according to the invention and the diazonium salt in a concentration of $10^{-4}$ to $10^{-1}$ mole/litre, in particular $10^{-3}$ to $10^{-2}$ mole/litre.

When filter paper is used as the matrix, the finished test papers can be used as such or they can be stuck onto handles in a manner which is known per se or, preferably, sealed between plastics and fine-mesh networks, for example according to DE-OS (German Published Specification) 2,118,455.

To produce test strips coated with film, preferably all the reagents are introduced into the solution or dispersion of a film-forming substance, such as, for example, a polyvinyl ester or polyamide, and are homogeneously mixed. A thin layer of the mixture is brushed onto a carrier made of plastic and dried. After drying, the film-coated test strips thus produced are cut and can be used as such or stuck onto handles in a manner which is known per se, or, for example, sealed between plastics and fine-mesh networks according to DE-OS (German Published Specification) 2,118,455.

A diagnostic agent according to the invention for the detection of esterolytic and/or proteolytic enzymes, in particular leucocyte enzymes, can be prepared in the form of powder mixtures or reagent tablets by adding the usual pharmaceutical additives to the abovementioned constituents of the test agent and granulating the mixture. Examples of additives of this type are carbohydrates, such as, for example, mono-, oligo- or poly-saccharides, or sugar-alcohols, such as, for example, mannitol, sorbitol or xylitol, or other soluble inert compounds, such as polyethylene glycols or polyvinylpyrrolidone. The powder mixtures or reagent tablets have, for example, a final weight of about 50–200 mg, oreferably 50–80 mg.

To prepare lyophilisates with a total weight of in each case about 5–20 mg, preferably about 10 mg, a solution which, in addition to all the reagents required for the test, contains the usual structure-forming agents, such as, for example, polyvinylpyrrolidone, and if appropriate other fillers, such as, for example, mannitol, sorbitol or xylitol, is freeze-dried.

A diagnostic agent according to the invention in the form of a solution preferably contains all the reagents required for the test. Possible solvents are water and mixtures of water with a water-soluble organic solvent, such as, for example, methanol, ethanol, acetone or dimethylformamide. For storage reasons, it may be advantageous to divide the reagents required for the test into two or more solutions, which are only brought together during the actual investigation.

The diagnostic agents thus prepared permit, after immersion in the body fluid to be investigated or after addition to the body fluid in question, rapid and simple detection of the presence of esterolytic and/or proteolytic enzymes, in particular leucocyte enzymes, via colour formation, which can be measured visually or photometriLe for example by reflectance photometry or in a cell. Since the activity of the leucocyte enzymes per cell can be regarded as an essentially constant parameter, the leucocyte concentration of the body fluid investigated can be determined from the intensity of the colour formation. Both intact and lysed leucocytes are thereby recorded with the diagnostic agent according to the invention, since the activity of the leucocyte enzymes is fully retained even after lysis of the leucocytes. Consequently, no lysis error occurs.

The following examples serve to illustrate the present invention. Unless indicated otherwise, the amounts given are to be understood as parts by weight or percentages by weight.

Preparation of the N-tosyl-L-alanyl esters:

The esters were in each case prepared, for example, by reacting N-tosyl-L-alanyl chloride with the phenols in absolute methyl ethyl ketone or absolute toluene in the presence of powdered potassium carbonate. After stirring at about 55° C. for 6 to 12 hours, between 40 and 70% of the phenol had reacted. The molar ratio of phenol:$K_2CO_3$: acid chloride was usually 1:1.5:1.5. The pH value was about 7 throughout the entire reaction time. For working up, the potassium carbonate was filtered off at 50° C. and the solvent was then distilled off in vacuo. The product was purified via column chromatography with silica gel-eluant (for example petroleum ether:acetone=about 9:1) and subsequent recrystallisation.

p-Tosyl-L-alanine

Literature: E. Fischer and W. Lipschitz, B. 48, 362 (1915).

83.7 g (0.93 mole) of L-alanine are dissolved in 465 ml of approximately 2 N sodium hydroxide solution. 186 g (0.976 mole) of p-toluenesulphonyl chloride are added to the solution in portions at 70°–72° C. in the course of 20 minutes. During the addition of the sulphonyl chloride, the reaction mixture is kept at pH 10 with approximately 2 N sodium hydroxide solution by means of an automatic titrator; 560 ml of 2 N sodium hydroxide solution are consumed here. When the pH of the reaction mixture no longer changes, the mixture is cooled to 15°–5° C. and brought to pH 3 with 37% strength hydrochloric acid. The product which has separated out is filtered off with suction and the moist filter cake is recrystallised from 2,350 ml of water.

Yield: 185.5 g (82% of theory) of L-p-tosylalanine of melting point 132°–135° C.

p-Tosyl-L-alanyl chloride 158.1 g (0.65 mole) of p-tosyl-L-alanine are stirred in 350 ml of thionyl chloride at 40° C., until a clear solution has formed. The excess thionyl chloride is then distilled off under a waterpump vacuum. The residue in the flask is taken up in 300 ml of distilled toluene. A clear, slightly yellowish solution is obtained, which is poured into 900 ml of stirred ligroin. The acid chloride precipitates. The following day, it is filtered off with suction, washed with light gasolene and dried in a vacuum desiccator over calcium chloride/potassium hydroxide.

Yield: 155 g (91% of theory) of almost colourless crystals of melting point 81°–83° C.

5-[N-Toluene-4″-sulphonyl)-L-alanyloxy]-1,2-benzisothiazole 3.02 g of 5-hydroxy-1,2-benzisothiazole are warmed to 55° C. in 150 ml of absolute methyl ethyl ketone together with 3 g of anhydrous $K_2CO_3$, with stirring. A total of 6 g of N-tosyl-L-alanyl chloride is added in portions at 55° C. in the course of 6 hours, with thorough stirring. The mixture is then subsequently stirred at 55° C. for a further 2 hours. After cooling, the $K_2CO_3$ is filtered off and the solvent is then evaporated off in a rotary evaporator. The crude product was purified by high oressure liquid chromatography on a silica gel column. Eluant: hexane:methylene chloride:n-butanol=40:8:1. Detection of the desired product: UV at 254 nm. For an application amount of $3 \times 100$ mg, a total of 100 mg of 5[N-(toluene-4″-sulphonyl)-L-alanyloxy]-1,2-benzisothiazole were isolated.

5-[N-(Toluene-4″-sulphonyl)-L-alanyloxy]-indazole 0.6 g of 5-hydroxy-indazole is taken in 50 ml of absolute methylene chloride, together with 1.2 g of absolute pyridine, at 40° C. 1.5 g of N-tosyl-L-alanyl chloride, dissolved in 25 ml of absolute methylene chloride, are added dropwise at 40° C. in the course of 3 hours. The mixture is then subsequently stirred at 40° C. for a further 2 hours. After cooling, the methylene chloride solution is washed 3 times with 100 ml of 2% strength citric acid each time. The methylene chloride phase is then dried over sodium sulphate and, after the drying agent has been filtered off, is evaporated in vacuo at room temperature. The residue thus obtained is purified by column chromatography on silica gel, eluant: petroleum ether: acetone 6:4. After the solvent has been evaporated off from the desired fraction, 0.4 g of 5-[N-toluene-4″-sulphonyl-L-alanyloxy]-indazole is obtained.

The following substrates are obtained in an analogous manner by reacting the corresponding hydroxybenzisothiazoles and hydroxyindazoles of the formula (II) with the particular N-protected aminoacids or reactive aminoacid derivatives: 4-[N-(toluene-4″-sulphonyl)-L-alanyloxy]-1,2-benzisothiazole, 4-[N-(toluene-4″-sulphonyl)-L-valyloxy]-1,2-benzisothiazole, 5-[N-(t-butyloxycarbonyl)-L-alanyloxy]-1,2-benzisothiazole, 6-[N-benzyloxycarbonyl)-L-alanyloxy]-indazole, 5-[N-methylsulphonyl-L-lysyloxy]indazole, 4-[N-(4″-methoxybenzenesulphonyl)-L-alanyloxy]indazole, 5-[N-benzyloxycarbonyl-O-acetyl-L-tyrosyloxy]2,1-benzisothiazole, 5-[N-benzenesulphonyl-L-phenylalanyloxy]-1,2-benzisothiazole and 6-[N-benzyloxycarbonyl-L-valyloxy]-indazole.

EXAMPLE 2

Filter paper (for example Eaton and Dikeman 205) is impregnated with the following solutions in succession and then dried at 60° C.

Solution 1

0.1 Molar tris-(hydroxymethyl)-aminomethane buffer (ph 8.4), 3% of polyvinylpyrrolidone and 2.5% of polyL-Arg. Solvent: water.

Solution 2

$7.5 \times 10^{-3}$ Mole/liter of 5-[N-(toluene-4″-sulphonyl)-L-alanyloxy]-1,2-benzisothiazole and $1 \times 10^{-2}$ mole/liter of 2,4-dimethoxy-benzenediazoniumtetrafluoborate. Solvent: anhydrous acetone.

A pale yellow-coloured test paper which becomes red-brown in colour when immersed in urines containing leucocytes is obtained.

EXAMPLE 3

A tablet containing 5 mg of 5-[N-(toluene-4″-sulphonyl)-L-alanyloxy]-1,2-benzisothiazole, 5 mg of 2,4-dimethoxy-benzenediazoniumtetrafluoforate, 4 mg of potassium dihydrogen phosphate, 80 mg of disodium hydrogen phosphate dihydrate, 6 mg of poly-L-Lys and 110 mg of mannitol is mixed with 5 ml of a urine containing leucocytes. The urine sample becomes red-brown in colour.

What is claimed is:

1. Compounds of the general formula

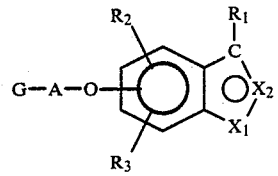

in which $X_1$ and $X_2$ are identical or different and are nitrogen or sulphur, with the proviso that $X_1$ and $X_2$ are not simultaneously sulphur;

$R_1$ is hydrogen or a branched alkyl group which has 1 to 6 carbon atoms which can be substituted by halogen or hydroxyl;

$R_2$ and $R_3$ are identical or different and are hydrogen, $C_1$–$C_6$-alkyl groups, $C_1$–$C_6$-alkoxy groups, $C_1$–$C_6$-acyl groups, halogen, trifluoromethyl, nitro, $SO_3H$, cyano, $C_1$–$C_8$-acylamino groups, $C_1$–$C_6$-dialkylamino groups or $C_6$–$C_{10}$-aryl groups, which can in turn be further substituted by $C_1$–$C_6$-alkyl groups, $C_1$–$C_6$-alkoxy group, halogen, cyano, nitro, trifluoromethyl, $SO_3H$, $C_1$–$C_6$-acyl groups or $C_1$–$C_6$-dialkylamino groups, or $R_2$ and $R_3$ together form a fused-on aromatic ring which can in turn be substituted by 1 to 2 radicals $R_2$;

A is a naturally occurring amino acid radical or a peptide radical of 2 to 8 naturally occurring amino acids; and G is hydrogen or a nitrogen-protective group which is usual in peptide chemistry or derived from such a group.

2. Compounds according to claim 1, wherein $X_1$ is sulphur and $X_2$ nitrogen.

3. Compounds according to claim 1 or 2, characterized in that $R_1$ is hydrogen.

4. Compounds according to claim 1 or 2, wherein $R_2$ and $R_3$, which are identical or different, are hydrogen, $C_1$–$C_2$-alkyl, $C_1$–$C_2$-alkoxy, halogen, $C_1$–$C_4$-dialkylamino groups or benzene radicals.

5. Compounds according to claim 4, wherein $R_2$ and $R_3$ are hydrogen or together form a fused-on benzene ring.

6. Compounds according to claim 5, wherein the ester grouping is in the 5-position.

* * * * *